(12) United States Patent
Menegassi de Almeida et al.

(10) Patent No.: US 12,297,158 B2
(45) Date of Patent: May 13, 2025

(54) PROCESS FOR PRODUCING COMPOUNDS, INCLUDING TRIPTANE BY AN ALCOHOL COUPLING REACTION

(71) Applicant: Petróleo Brasileiro S.A.—Petrobras, Rio de Janeiro (BR)

(72) Inventors: Rafael Menegassi de Almeida, Rio de Janeiro (BR); Carlos Rene Klotz Rabello, Rio de Janeiro (BR); Anderson Rouge dos Santos, Duque de Caxias (BR); Edimilson Jesus de Oliveira, Niterói (BR)

(73) Assignee: Petróleo Brasileiro S.A.—Petrobras, Rio de Janeiro (BR)

( * ) Notice: Subject to any disclaimer, the term of this patent is extended or adjusted under 35 U.S.C. 154(b) by 219 days.

(21) Appl. No.: 17/779,827

(22) PCT Filed: Nov. 19, 2020

(86) PCT No.: PCT/BR2020/050487
§ 371 (c)(1),
(2) Date: May 25, 2022

(87) PCT Pub. No.: WO2021/102541
PCT Pub. Date: Jun. 3, 2021

(65) Prior Publication Data
US 2023/0002295 A1    Jan. 5, 2023

(30) Foreign Application Priority Data

Nov. 26, 2019   (BR) .................. 10 2019 024934 0

(51) Int. Cl.
*C07C 1/22*         (2006.01)
*B01J 21/04*        (2006.01)
(Continued)

(52) U.S. Cl.
CPC ................. *C07C 1/22* (2013.01); *B01J 21/04* (2013.01); *B01J 23/72* (2013.01); *B01J 23/883* (2013.01);
(Continued)

(58) Field of Classification Search
CPC .......... B01J 21/04; B01J 23/72; B01J 23/883; C07C 1/22; C07C 29/34
See application file for complete search history.

(56) References Cited

U.S. PATENT DOCUMENTS

| 453,375 A | 6/1891 | Creswell |
| 1,755,692 A | 4/1930 | Herrmann et al. |

(Continued)

FOREIGN PATENT DOCUMENTS

| WO | 2012035772 A1 | 3/2012 |
| WO | 2021102541 A1 | 6/2021 |

OTHER PUBLICATIONS

Wibaut et al. (1939) "A Study on the Preparation and the Physical Constants of a Number of Alkanes and Cycloalkanes", Receuil des Travaux Chimiques des Pays-Bas, 58(4):329-377.

(Continued)

*Primary Examiner* — Sharon Pregler
(74) *Attorney, Agent, or Firm* — Mintz, Levin, Cohn, Ferris, Glovsky and Popeo, P.C.

(57) ABSTRACT

The present invention relates to a method for the production of molecules with seven carbons constituted by a chain of four carbons with three methyl branches, primarily triptane (2,2,3-trimethylbutane), by alcohol coupling reaction (Guerbet reaction), resulting in an alcohol with a four-carbon chain with three methyl branches, which is transformed into triptane. The importance of this method stems from the fact that triptane is the hydrocarbon with the greatest capacity to resist compression without ignition and can be used in (Continued)

unleaded aviation gasolines and in the formulation of high-octane automotive gasolines.

25 Claims, 1 Drawing Sheet

(51) Int. Cl.
  *B01J 23/72* (2006.01)
  *B01J 23/883* (2006.01)
  *C07C 29/34* (2006.01)

(52) U.S. Cl.
  CPC .......... *C07C 29/34* (2013.01); *C07C 2523/28* (2013.01); *C07C 2523/755* (2013.01); *C07C 2523/883* (2013.01)

(56) References Cited

U.S. PATENT DOCUMENTS

| | | |
|---|---|---|
| 1,821,667 A | 9/1931 | Emmet |
| 1,910,582 A | 5/1933 | Pieter |
| 1,992,480 A | 2/1935 | Otto et al. |
| 1,999,196 A | 4/1935 | Lazier |
| 2,004,350 A | 6/1935 | Scott |
| 2,050,788 A | 8/1936 | Otto et al. |
| 2,050,789 A | 8/1936 | Otto et al. |
| 2,064,254 A | 12/1936 | Otto et al. |
| 2,094,297 A | 9/1937 | Philip et al. |
| 2,404,537 A | 7/1946 | Louis et al. |
| 2,404,927 A | 7/1946 | Louis et al. |
| 2,407,584 A | 9/1946 | Stover |
| 2,417,119 A | 3/1947 | Miller et al. |
| 2,422,670 A | 6/1947 | Vladimir et al. |
| 2,422,671 A | 6/1947 | Vladimir et al. |
| 2,422,672 A | 6/1947 | Vladimir et al. |
| 2,422,674 A | 6/1947 | Vladimir et al. |
| 2,422,675 A | 6/1947 | Vladimir et al. |
| 2,436,923 A | 3/1948 | Vladimir |
| 2,453,144 A | 11/1948 | Lovell et al. |
| 2,457,866 A | 1/1949 | Carter |
| 2,485,897 A | 10/1949 | Marschner |
| 2,492,984 A | 1/1950 | Grosse et al. |
| 2,583,739 A | 1/1952 | Kemp et al. |
| 2,593,009 A | 4/1952 | Alfred et al. |
| 2,645,667 A | 7/1953 | Burgoyne |
| 2,645,668 A | 7/1953 | Burgoyne et al. |
| 2,762,847 A | 9/1956 | Miller et al. |
| 2,829,177 A | 4/1958 | Cull et al. |
| 2,836,628 A | 5/1958 | Miller |
| 2,862,013 A | 11/1958 | Miller et al. |
| 2,865,963 A | 12/1958 | Garetson et al. |
| 2,971,033 A | 2/1961 | Farrar |
| 3,047,630 A | 7/1962 | Emest |
| 3,119,880 A | 1/1964 | John et al. |
| 3,328,470 A | 6/1967 | Poe |
| 3,479,412 A | 11/1969 | Pregaglia et al. |
| 3,586,729 A | 6/1971 | Juguin et al. |
| 3,651,168 A | 3/1972 | Stoessel et al. |
| 3,860,664 A | 1/1975 | Yates |
| 3,862,993 A | 1/1975 | Yates et al. |
| 3,862,994 A | 1/1975 | Yates |
| 3,864,407 A | 2/1975 | Yates |
| 3,916,015 A | 10/1975 | Yates |
| 3,917,722 A | 11/1975 | Yates |
| 3,969,427 A | 7/1976 | Bell et al. |
| 3,979,466 A | 9/1976 | Yates |
| 4,011,273 A | 3/1977 | Abend et al. |
| 4,059,646 A | 11/1977 | Wald et al. |
| 4,059,647 A | 11/1977 | Wald et al. |
| 4,518,810 A | 5/1985 | Matsuda et al. |
| 4,681,868 A | 7/1987 | Budge et al. |
| 4,987,270 A | 1/1991 | Bott et al. |
| 5,068,469 A | 11/1991 | Young et al. |
| 5,095,156 A | 3/1992 | Radlowski et al. |
| 5,159,125 A | 10/1992 | Hagen |
| 5,300,695 A | 4/1994 | Radlowski |
| 5,493,064 A | 2/1996 | Vanderspurt et al. |
| 5,559,275 A | 9/1996 | Barger |
| 5,811,602 A | 9/1998 | Vanderspurt et al. |
| 6,034,141 A | 3/2000 | Vanderspurt et al. |
| 7,119,125 B1 | 10/2006 | Olenick et al. |
| 7,332,638 B2 | 2/2008 | Boesveld et al. |
| 7,642,392 B2 | 1/2010 | Kay et al. |
| 7,700,810 B2 | 4/2010 | Kourtakis et al. |
| 7,700,812 B2 | 4/2010 | Kourtakis et al. |
| 7,700,813 B2 | 4/2010 | Kourtakis et al. |
| 7,705,192 B2 | 4/2010 | Kourtakis et al. |
| 7,825,287 B2 | 11/2010 | Ahn et al. |
| 7,833,295 B2 | 11/2010 | Clark |
| 7,897,034 B2 | 3/2011 | De et al. |
| 8,071,822 B2 | 12/2011 | Ozer et al. |
| 8,071,823 B2 | 12/2011 | Ozer et al. |
| 8,232,437 B2 | 7/2012 | Clark et al. |
| 8,318,989 B2 | 11/2012 | Kourtakis et al. |
| 8,318,990 B2 | 11/2012 | Tanaka et al. |
| 8,398,728 B2 | 3/2013 | Ozer et al. |
| 8,431,753 B2 | 4/2013 | Ozer et al. |
| 8,536,389 B2 | 9/2013 | Parker et al. |
| 8,603,201 B2 | 12/2013 | Tsuchida et al. |
| 8,809,594 B2 | 8/2014 | Norman et al. |
| 8,962,897 B2 | 2/2015 | Zhang et al. |
| 9,018,427 B2 | 4/2015 | Gadewar et al. |
| 9,024,090 B2 | 5/2015 | Zhang et al. |
| 10,214,470 B2 * | 2/2019 | Dubois ............... C07C 2/06 |
| 2016/0108323 A1 * | 4/2016 | Marshall ............. C10G 3/45 585/733 |

OTHER PUBLICATIONS

Ahn et al. (2009) "Selective Homologation Routes to 2,2,3-trimethylbutane on Solid Acids", Angewandte Chemie International Edition, 48(21):3814-3816.

Burk et al. (1985) "The Rhodium-promoted uGerbet Reaction: Part II. 1 Secondary Alcohols and Methanol as Substrates", Journal of Molecular Catalysis, 33(1):15-21.

Cao et al. (1988) "Lumped Kinetic Model For Propene-Butene Mixtures; Oligomerization on a Supported Phosphoric Acid Catalyst", Applied Catalysis, 41:301-312.

Cardona et al. (Aug. 1995) "Reactions Involved in the Alkylation of Iobutane with 2-butene and with Propene on a USHY Zeolite", 128(2):243-257.

Carlini et al. (May 2005) "Guerbet Condensation of Methanol with N-Propanol to Isobutyl Alcohol over Heterogeneous bifunctional catalysts Based on Mg—Al Mixed Oxides Partially Substituted by Different Metal Components", Molecular Catalysis, 232(s 1-2):13-20.

Carlini et al. (Jun. 2003) "Selective Synthesis of Isobutanol by means of the Guerbet Reaction: Part 2. Reaction of methanol/ethanol and methanol/ethanol/n-propanol Mixtures Over Copper Based/MeONa Catalytic Systems", Journal of Molecular Catalysis A: Chemical, 200(1-2):137-146.

Carlini et al. (Oct. 2003) "Selective Synthesis of Isobutanol by Means of the Guerbet Reaction: Part 3: Methanol/n-propanol Condensation by using Bifunctional Catalytic Systems based on Nickel, Rhodium and Ruthenium Species with Basic Components", Molecular Catalysis, 206(1-2):409-418.

Eisele et al. (2013) ""Propene," in: Ullmann's Encyclopedia of Industrial Chemistry", 30:p. 281. (14 pages).

Farberow et al. (2017) "Exploring Low-Temperature Dehydrogenation at Ionic Cu Sites in Beta Zeolite to Enable Alkane Recycle in Dimethyl Ether Homologation", ACS Catalysis, 7(5):3662-3667.

Haensel et al. (1947) "Selective Demethylation of Paraffin Hydrocarbons", Industrial & Engineering Chemistry Research, 39(7):853-857.

Ipatieff et al. (1945) "Heptenes and Heptanes from Propylene and Butylenes", Industrial & Engineering Chemistry Research, 37(4):362-364.

Ipatieff et al. (1939) "Reaction of Propene with Isoolefins in the Presence of Sulfuric Acid", Journal of the American Chemical Society, 61(7):1825-1826.

(56) References Cited

OTHER PUBLICATIONS

Kettering, Charles F. (1944) "Effect of Molecular Structure of Fuels on Power and Efficiency of Internal Combustion Engines", Industrial & Engineering Chemistry Research, 36(12):1079-1085.
Klerk (2011) "Key Catalyst Types for the Efficient Refining of Fischer-tropsch Syncrude: Alumina And Phosphoric Acid", Catalysis, 2011, 23:1-49.
Kozlowski et al. (2013) "Heterogeneous Catalysts for the Guerbet Coupling of Alcohols", ACS Catalysis, 3(7):1588-1600.
Miller et al. (1948) "Methylation of Olefins with Methyl Chloride", Industrial & Engineering Chemistry Research, 40(6):1138-1150.
O'Lenick Jr., J.A. (2001) "Guerbet Chemistry", Journal of Surfactants and Detergents, 4(3):311-315.
Shimura et al. (2013) "Self-coupling of Secondary Alcohols by Ni/CeO2 Catalyst", Applied Catalysis A: General, 462-463:137-142.
Splitter et al. (Jan. 2016) "A Historical Analysis of the Co-evolution of Gasoline Octane Number and Spark-Ignition Engines", Frontiers in Mechanical Engineering, 1(16):22 pages.
Suarez et al. (2013) "Vapor-Phase Methanol and Ethanol Coupling Reactions on CuMgAl Mixed Metal Oxides", Applied Catalysis A: General, 455:234-246 (40 Pages).
Veibel et al. (1967) "On the mechanism of the Guerbet Reaction", Tetrahedron, 23(4):1723-1733.

\* cited by examiner

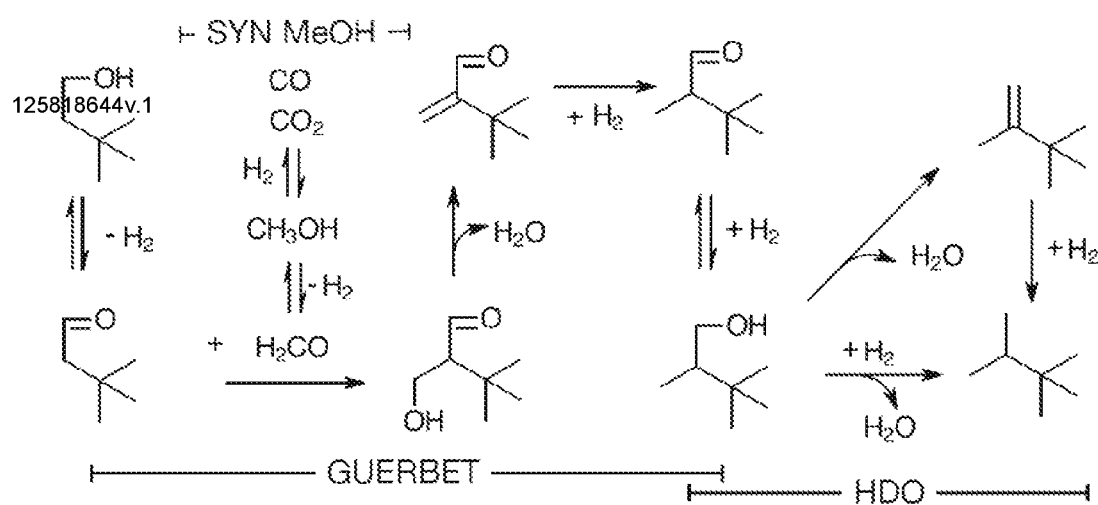

PROCESS FOR PRODUCING COMPOUNDS, INCLUDING TRIPTANE BY AN ALCOHOL COUPLING REACTION

CROSS-REFERENCE TO RELATED APPLICATIONS

This application is a national phase application, filed under 35 U.S.C. § 371, of PCT International Patent Application No. PCT/BR2020/050487, filed Nov. 19, 2020, and claims benefit of and priority to Brazilian application BR 10 2019 024934 0, filed on Nov. 26, 2019, the disclosures of all of which are incorporated herein by reference in their entirety.

FIELD OF THE INVENTION

The present invention relates to a method for the production of molecules with seven carbons constituted by a chain of four carbons with three methyl branches, primarily triptane (2,2,3-trimethylbutane), by alcohol coupling reaction (Guerbet reaction), resulting in an alcohol with a four-carbon chain with three methyl branches, which is transformed into triptane. The importance of this method stems from the fact that triptane is the hydrocarbon with the greatest capacity to resist compression without ignition and can be used in unleaded aviation gasolines and in the formulation of high-octane automotive gasolines.

BACKGROUND OF THE INVENTION

Gasoline is a fuel for Otto cycle engines, in which the property of resistance to detonation is essential, both in aviation and automotive applications. A need exists in the prior art to obtain components with a high capacity for resisting detonation, which is expressed by octane measurements, especially in engines with air compression prior to mixing with the fuel. The historical trend has been toward higher-octane gasoline and the premium gasoline market, which represents about 20% of the gasoline consumed in the USA (D. Splitter, A. Pawlowski, R. Wagner, "A historical analysis of the co-evolution of gasoline octane number and spark-ignition engines," Frontiers Mech. Eng. 1 (2016) 16).

Airplanes with Otto cycle engines operate in a high compression ratio condition with turbocharging or air supercharging, rendering them susceptible to premature detonation. One way to increase the octane rating is to use additives such as tetraethyl lead (TEL). However, due to environmental and health problems resulting from the release of lead in combustion, use thereof is being limited in accordance with ASTM D910-17a, and formulations of unleaded aviation gasoline are being developed. For this, components with a high capacity to withstand compression without detonation, such as triptane (2,2,3-trimethylbutane), are required.

The literature shows that the composition of gasolines with triptane makes it possible to substantially increase the indicated mean effective pressure (IMEP) with gains in power and efficiency before premature detonation, with unleaded triptane being superior to leaded isooctane under the conditions studied. It is reported that, with aviation gasoline containing the same octane rating of 100 and 60 vol % triptane, it was possible to obtain 2500 hp in an airplane engine, compared to 1500 hp with normal 100-octane aviation gasoline without triptane (C. F. Kettering, "Effect of molecular structure of fuels on power and efficiency of internal combustion engines," Ind. Eng. Chem. 36 (1944) 1079-1085).

In order to make this strategy viable, the prior art describes several compositions with triptane. For example, U.S. Pat. No. 2,485,897 describes a mixture of triptane with cyclopentane to obtain gasoline in which the compound contains at least 25 vol % triptane and 75% cyclopentane.

Given the difficulty in obtaining triptane, gasoline formulations containing less and less triptane have been proposed in the prior art. U.S. Pat. No. 7,897,034 describes a tetraethyl lead-free aviation gasoline formulation containing up to 10% triptane. Similarly, U.S. Pat. Nos. 7,833,295, 8,232,437, and 8,536,389 describe gasoline formulations containing at least 5 vol % triptane or 2,2,3-trimethylpentane.

The usefulness of a triptane production method for use in Otto cycle fuel formulations is thus clear from the prior art. As will be apparent from the multiplicity of techniques described below, various attempts have been made to produce the component on a large scale.

The prior art describes a method for producing triptane by reacting pinacolone with methyl magnesium iodide in the Grignard reaction in order to transform the ketone into alcohol, followed by dehydration and hydrogenation (J. P. Wibaut, H. Hoog, S. L. Langedijk, J. Overhoff, J. Smittenberg, "A study on the preparation and the physical constants of a number of alkanes and cycloalkanes," Receuil des Travaux Chimiques des Pays-Bas 58(4): 329-377, 1939).

In the same vein, documents U.S. Pat. Nos. 2,417,119, 2,453,144, and Miller and Lovell (V. Miller, W. Lovell, "Methylation of olefins with methyl chloride," Industrial Eng Chem. 40 (1948) 1138-1150) describe the production of triptane by means of olefin methylation with methyl chloride in the presence of metal oxide (CaO) in order to capture chlorine. The mentioned production route requires a specific olefin (2,3-dimethyl-2-butene) with one methylation, or it is possible to start from 2-methyl-2-butene with two methylations.

Thus, despite the detailed description of triptane production methods, there are many limiting factors in these documents, including the limited availability of the specific C5= or C6= olefin (trimethylethylene or tetramethylethylene) and the use of chloromethane and CaO, solid, as reagents.

In the same sense, similar processes involving halogenation and chlorinated compounds are described in U.S. Pat. Nos. 2,404,927 and 2,404,537, but the use of halogenated compounds is industrially undesirable.

Another method that is described in the prior art is the hydrodemethylation of C8 isoparaffin, obtained from the heavy alcoholic fraction, as dictated by U.S. Pat. Nos. 2,422,670, 2,422,671, 2,422,672, 2,422,674, 2,422,675, and Haensel and Ypatieff (V. Haensel, V. Ipatieff, "Selective demethylation of paraffin hydrocarbons," Industrial Eng. Chem. 39 (1947) 853-857). On account of the exothermicity, consideration has been given to removing heat with water, as the U.S. Pat. No. 2,436,923 teaches, but reformation reactions of the methane that is produced also occur, and the possibility of temperature excursions is not eliminated.

Still in relation to the production of triptane, additional methodologies involve the isomerization of streams with seven carbons. However, the equilibrium only favors triptane at low temperatures, preferably below 0° C. In these methods, isomerization under low-temperature conditions can be catalyzed with superacids, either homogeneous or heterogeneous, as is taught in U.S. Pat. Nos. 2,583,739 and 7,332,638. Although the aforementioned method presents an alternative for obtaining triptane, the low yield and the issues involved in the recovery and deactivation of catalysts make it unattractive industrially.

In an alternative methodology to those described in the prior art, it is desirable to produce triptene via the oligomerization of isobutene with propylene followed by hydrogenation to triptane, as is taught by Ypatieff et al. and Ypatieff and Schaad (V. N. Ipatieff, H. Pines, B. S. Friedman, "Reaction of propene with isoolefins in the presence of sulfuric acid," *J. Am. Chem. Soc.* 61 (1939) 1825-1826; V. N. Ipatieff, R. E. Schaad, "Heptenes and heptanes from propylene and butylenes," *Ind. Eng. Chem.* 37 (1945) 362-364). However, the reaction produces a low yield of only 3% triptene. Even with catalysts other than sulfuric acid, such as phosphoric acid, dimethylpentenes are preferably formed, as is taught in documents U.S. Pat. Nos. 3,651,168, 3,586,729, Klerk (A. de Klerk, "Key catalyst types for the efficient refining of Fischer-Tropsch syncrude: alumina and phosphoric acid," *Catalysis* (23), 2011), and Cao et al. (G. Cao, A. Viola, R. Baratti, M. Morbidelli, L. Sanseverino, M. Cruccu, "Lumped kinetic model for propene—butene mixtures; oligomerization on a supported phosphoric acid catalyst," *Applied Catalysis* 41 (1988) 301-312).

The alkylation reaction of isobutane with propylene could be a candidate for producing triptane. It is known, however, that in the industrial process of alkylation with HF or $H_2SO_4$, the primary products are 2,3- and 2,4-dimethylpentanes, as is taught by Eisele and Killpack (P. Eisele, R. Kilipack, *ULLMANN'S Encyclopedia of Industrial Chemistry-Propene*. vol. 30, (2013) p. 281), Asinger (Asinger, F., *Mono-Olefins: Chemistry and Technology*, Pergamon Press, 1968), and Albright (Albright, L. F. et al.; *Industrial and Laboratory Alkylations*, ACS Symposium Series, A C S, 1977).

Likewise, the use of zeolitic catalysts in the alkylation of isobutane with propylene results in triptane contents of less than or equal to 0.1%, as is taught by Cardona et al. (F. Cardona, N. S. Gnep, G. Szabo, P. Nascimento, "Reactions involved in the alkylation of isobutane with 2-butene and with propene on a USHY zeolite," 128 (1995) 243-257). This is due to the fact that the formation of triptane through alkylation of isobutane with propylene is thermodynamically unfavorable, requiring pressures of 200 to 300 bar and temperatures of above 400° C. in order to achieve yields in the range of 10% using chlorinated compounds, brominated compounds, or $CO_2$ as catalysts, as is described in U.S. Pat. No. 2,407,584.

The subsequently published documents U.S. Pat. Nos. 2,492,984, 3,969,427, 4,059,646, 4,059,647, and 7,642,392 teach the homologation reaction of methanol or dimethyl ether (DME) for the production of triptane in Zn halides and other metals. Likewise, due to the difficulties with routes involving hydrated fused salts ($ZnCl_2$, $ZnI_2$, etc.), a heterogeneous homologation route via acid catalysis was sought, as is described in WO/PCT/2009063177, WO/PCT/2009063178, U.S. Pat. No. 7,825,287, and Ahn et al. (J. H. Ahn, B. Temei, E. Iglesia. "Selective homologation routes to 2,2,3-trimethyibutane on solid acids," *Angewandte Chemie Int. Ed.* 48 (2009) 3814-3816).

Attempts have also been made to add larger compounds to the chain, such as (intermediate) iC4, aided by an additional dehydrogenation function in the catalyst, in order to accelerate the methanol (and DME) homologation reaction, as is taught by Farberow et al. (C. A. Farberow, S. Cheah, S. Kim, J. T. Miller, J. R. Gallagher, J. E. Hensley, J. A. Schaidle, D. A. Ruddy, "Exploring low-temperature dehydrogenation at ionic Cu sites in beta zeolite to enable alkane recycle in dimethyl ether homologation, *ACS Catal.* 7 (2017) 3662-3667).

However, there are still unresolved issues inherent to the use of acid catalysts in homologation, primarily in relation to product degradation and catalyst deactivation, limiting the application of this method to date.

From this perspective, the alcohol coupling reaction, or Guerbet reaction, used in the present invention is a type of carbon-carbon chain construction that does not have the drawbacks of acid catalysis. Such an alcohol coupling reaction, as is taught by Veibel and Nielsen (Veibel, S.; Nielsen, J. I. (1967), "On the mechanism of the Guerbet reaction," *Tetrahedron,* 23(4), 1723-1733), takes place in steps of dehydrogenation of alcohol hydroxyls to carbonyls plus 2 $H_2$, generating primary alcohols, aldehydes, and secondary alcohols, ketones. The dehydrogenation products of said alcohols react with one another in aldol condensation, with elimination of water. Then the unsaturated ketone (enone) formed is hydrogenated, resulting in the higher-chain Guerbet alcohol. In a Guerbet reaction catalyst, both dehydrogenating/hydrogenating and basic functions are required in order to achieve aldol condensation.

Guerbet alcohols, which result from the coupling of alcohols, are primary or secondary, although most alcohols produced from primary adducts also result in primary alcohols, and the properties conferred by the branched structure of the alcohol enable them to find application in various industries in addition to the use thereof as solvents. In particular, the properties of the alcohol formed are: low toxicity, liquid at extremely low temperatures, low volatility, good lubricant, good oxidative stability, excellent initial color, biodegradability, inter alia, as is taught by OLenick (OLenick, A. J. (2001), "Guerbet chemistry," *Journal of Surfactants and Detergents,* 4(3), 311-315).

As mentioned, alcohols from the alcohol coupling reaction, or Guerbet reaction, can be formed by combining alcohols from different chains, as is shown in documents U.S. Pat. Nos. 2,050,788, 3,479,412, 5,493,064, and 7,705,192. Still in relation to the foregoing, diols can also be reacted with one another or with more alcohols, resulting in even larger chain sizes, as is explained by U.S. Pat. No. 7,119,125.

Aldol condensation is a reversible, endothermic, and equilibrium-limited reaction. Under the conditions usually employed in the prior art, it takes place with high selectivity. The presence of a hydrogenating function in the Guerbet catalyst plus excess $H_2$ helps the condensation reaction by hydrogenating the enone resulting from the aldol condensation.

In this scenario, it is worth noting that the Guerbet reactions typically develop at temperatures of greater than 200° C., in the range of 200 to 300° C., and the operating pressure is up to 200 bar. Furthermore, in this type of reaction, it is common practice to use autogenous pressure in a batch system at temperatures from 300° C. to 550° C. High temperatures are considered unnecessary, but low temperatures can be considered to be thermodynamic impediments for some reagents.

To maintain acceptable levels of temperature and pressure, several catalysts/basic systems and combinations with hydrogenating catalysts are described in the specialized literature, such as:

MgO, CaO, Ca(OH)$_2$, Ca phosphates: U.S. Pat. Nos. 1,755,692, 1,910,582, 1,992,480, 2,050,788, 2,050, 789, 2,645,667, 2,971,033, 5,095,156, 5,159,125, 8,318,989.

K, Na, Ba, Li, Mg, Ti, Zr—oxides, hydroxides, carbonates, phosphates (groups 1 and 2 in general). U.S. Pat.

Nos. 2,004,350, 2,762,847 (phosphates, basic), U.S. Pat. Nos. 2,971,033, 3,119,880, 3,328,470, 4,987,270, hydroxides (of Ca and K) are used in solution with alcohols. Still in relation to catalysts, metallic salts of carboxylic acids/fatty acids or alcoholates can also be used—U.S. Pat. Nos. 1,821,667, 2,836,628, 3,479,412 dehydrogenating/hydrogenating metals, such as Cu, Cr, Ni, Mn, Cd, Zn, Fe, Sn, Pb-reduced metals, oxides, hydroxides, salts such as halides, phosphates, carbonates, as described in the documents: U.S. Pat. Nos. 1,755,692, 1,992,480, 1,999,196, 2,004,350, 2,829, 177, 2,836,628, 3,916,015, 4,011,273, 4,518,810, 8,962,897, 9,018,427, 9,024,090;

Ni, Ru, Pd, Pt, Rh, Ir, Ag—oxides or salts, primarily in mixtures; documents U.S. Pat. Nos. 2,836,628, 2,862, 013, 3,047,630, 3,860,664, 3,916,015, 3,979,466, 8,318,990 relate to such use.

cerium and lanthanum: documents U.S. Pat. Nos. 5,559, 275, 5,300,695 describe them as potential catalysts.

mixtures of metals, salts, and support are described as—supported or unsupported—catalysts with a dehydrogenating and dehydrating effect by patent documents U.S. Pat. Nos. 2,064,254, 2,094,297, 2,645,667, 2,645, 668, 2,865,963, 2,971,033, 4,681,868, 5,559,275, 5,811,602, 6,034,141; V205 in anatase (Ti), U.S. Pat. No. 8,809,594, zeolites—basic, and with metal according to document U.S. Pat. No. 5,493,064, hydrotalcites (converted fully or partially to mixed oxides by heat treatment and removal of $H_2O$ and $CO_2$), with or without additional supported salts (in addition to those that make up hydrotalcite), with different intercalation anions: U.S. Pat. Nos. 7,700,810, 7,700,812, 7,700,813, 8,071,822, 8,071,823, 8,318,989, 8,603, 201.

hydroxyapatites: U.S. Pat. Nos. 8,431,753, 8,603,201.

Also worthy of mention are heterogeneous dehydrogenating catalysts used together with homogeneous basic catalysts as described in U.S. Pat. Nos. 3,119,880, 3,328,470, 3,862,993, 3,862,994, 3,864,407, 3,916,015, 3,917,722, 3,979,466.

Other basic catalysts such as the metallic oxides CaO, $K_2O$ are usually supported—for example on alumina or other supports such as Zr, basic zeolites, mixed oxides. The mixed oxides themselves are preferably used as a support.

In addition to metal oxides, carbides (US453375), silicates (such as lead, U.S. Pat. No. 4,011,273), or mixtures of solids, bases, and hydrogenating catalysts (e.g.: U.S. Pat. Nos. 2,971,033, 2,862,013, 2,836,628).

The literature teaches that hydrotalcites and hydroxyapatites and basic Ce supports are good catalysts for Guerbet condensation processes at milder conditions and with greater selectivity and yield, according to Kozlowski and Davis (Kozlowski, J. T., & Davis, R. J. (2013), "Heterogeneous catalysts for the guerbet coupling of alcohols," *ACS Catalysis*, 3(7), 1588-1600) and Shimura et al. (K. Shimura, K. Kon, S. M. A. Hakim Siddiki, K.-I. Shimizu, "Self-coupling of secondary alcohols by Ni/CeO$_2$ catalyst," *Appl. Catal. A. Gen.* 462-463 (2013) 137-142).

The prior art also describes that heterogeneous catalysts are preferred in the so-called Guerbet reaction, since the removal of homogeneous catalysts such as salts, hydroxides, and other catalysts and their byproducts (e.g. alkoxides) involves difficulty and a substantial number of operations.

In carrying out the aforementioned Guerbet process, the removal of water is an important aspect to be considered. In this respect, document U.S. Pat. No. 2,457,866 describes the process of removing water in order to reduce the formation of byproducts.

Documents U.S. Pat. Nos. 5,068,469, 5,159,125 describe the reaction of aldehydes (or ketones) with alcohols using the same conditions as in the Guerbet reaction. In such documents, it is taught that it is possible to start the reaction using already dehydrogenated alcohols (aldehydes/ketones) as reagents. If only aldehydes or ketones are used, the reaction is aldol condensation. Furthermore, U.S. Pat. No. 2,593,009 teaches the returning of unreacted adducts, alcohols, and the dehydrogenation products thereof (aldehydes/ketones) to the Guerbet reaction step.

The U.S. Pat. No. 8,809,594 teaches to decouple the reactions of dehydrogenation, aldol condensation, and hydrogenation in steps with different catalysts—whether in the same reactor or not. Intermediate or unreacted products can be recycled to the most appropriate reaction step, such as lower molecular-weight aldehydes/ketones for the condensation step and desired molecular-weight aldehydes/ketones for the hydrogenation step, as needed.

Another point to be highlighted is that the alcohol formed may be unstable in the very condition of the Guerbet reaction (e.g., dehydrating the olefin and hydrogenating), whereas the aldehyde/ketone is stable. Separating the dehydrogenating/hydrogenating function from the aldol condensation function may therefore be of interest for some compounds.

Due to the conditions employed (and the use of soluble bases, for example), the reactions usually take place in a liquid phase. However, a vapor phase reaction is possible for products of lower molecular weight and lower operating pressures with the presence of $H_2$, for example, added to the reaction. The U.S. Pat. No. 8,809,594 also teaches operation at pressures from 0 to 20 bar and the use of diluents such as $N_2$, $O_2$, air, argon, He, in addition to $H_2$.

The prior art also describes the production of dialkyl ethers from Guerbet alcohols, preferably those obtained from ethanol, preferably from a renewable source, according to the U.S. Pat. No. 8,398,728, with the main objective of dialkyl ethers being the use thereof as diesel substitutes, components, or additives.

The Guerbet reaction that is commonly known in the prior art is the self-condensation of alcohols. Cross-condensation, in which different alcohols react with one another, is less common. Even less common is the use of methanol as a reagent alcohol. Methanol does not self-condensate according to the Guerbet reaction mechanism, but it can condense with a second, larger alcohol. It can still promote other reactions such as Tishchenko, Cannizzaro, or decarboxylation reactions. Formaldehyde is considered to be extremely reactive, and it is surprising that it can still react in a reaction like Guerbet's.

Various reactions have been described in the prior art for obtaining Guerbet alcohols using methanol as one of the reagents (P. L. Burk, R. L. Pruett, K. S. Campo, "The rhodium-promoted Guerbet reaction. Part II. Secondary alcohols and methanol as substrates," *Journal of Molecular Catalysis*. 33 (1985) 15-21; Carlini, M. Di Girolamo, A. Macinai, M. Marchionna, M. Noviello, A. M. Raspolli Galletti, et al., "Selective synthesis of isobutanol by means of the Guerbet reaction. Part 2. Reaction of methanol/ethanol and methanol/ethanol/n-propanol mixtures over copper based/MeONa catalytic systems," *J. Mol. Catal. A*. 200 (2003) 137-146, 2003; C. Carlini, A. Macinai, M. Marchionna, M. Noviello, A. M. R. Galletti, G. Sbrana, "Selective synthesis of isobutanol by means of the Guerbet reaction. Part 3: Methanol/n-propanol condensation by using bifunctional catalytic systems based on nickel, rhodium and ruthenium species with basic components, *J. Mol. Catal. A.* 206 (2003) 409-418; C. Carlini, M. Marchionna, M. Noviello, A. M. Raspolli Galletti, G. Sbrana, F. Basile, C. Flego, M. Noviello, M. Noviello. "Guerbet condensation of methanol with n-propanol to isobutyl alcohol over heterogeneous bifunctional catalysts based on Mg—Al mixed oxides partially substituted by different metal components," *J. Mol. Catal. A.* 232 (2005) 13-20).

In a heterogeneous system of copper in a mixed oxide of Mg—Al (J. J. Bravo-Suarez, B. Subramaniam, R. V. Chaudhari, "Vapor-phase methanol and ethanol coupling reactions on CuMgAl mixed metal oxides," *Appl. Catal. A. Gen.* 455 (2013) 234-246), the Guerbet reaction with MeOH and EtOH reagents was also used. In this catalyst, for the reaction of methanol and n-propanol, the secondary reactions (dehydration, hydrogenolysis, decarboxylation) were more favored than the Guerbet reaction.

However, no documents were found in the prior art that describe the Guerbet reaction of C6 alcohols with methanol, much less any that describe the production of alcohol which, after dehydration and hydrogenation or hydrodeoxygenation, will produce triptane.

The present proposal thus describes the Guerbet reaction using catalysts with a basic function, offering advantages over catalytic processes that involve acid sites, such as less deactivation and carbon deposition, and potentially greater selectivity and yield.

To wit, despite the advantages associated with the use of triptane in gasoline compositions, the prior art fails to describe processes that are capable of producing triptane on a large scale to achieve an industrial scale. This issue is resolved by the present invention for the production of triptane by means of a Guerbet reaction that transforms six-carbon alcohols with methanol.

BRIEF DESCRIPTION OF THE INVENTION

The present invention encompasses the production of compounds containing seven carbons, with chains of four carbons containing three methyl branches, more specifically triptane (2,2,3-trimethylbutane). In addition to triptane, the present invention also encompasses the production of triptene (2,3,3-trimethyl-1-butene), triptanol (2,3,3-trimethylbutanol), and triptanal (2,3,3-trimethylbutyraldehyde).

The invention is based on a Guerbet reaction of an oxygenate containing 6 carbons, preferably 3,3-dimethyl-1-butanol (neohexanol) with methanol and/or mixtures of $H_2$ plus CO or $CO_2$ and mixtures thereof, preferably using a heterogeneous catalyst, combining a hydrogenating/dehydrogenating function and a basic function and resulting in a product that contains primarily triptanol plus triptanone.

The triptanol and triptanone produced in the first reaction step can optionally proceed to a second hydrodeoxygenation (HDO) reaction step. The hydrodeoxygenation reaction is usually catalyzed by a combination of an acid function and a hydrogenating function; the carbonyls are hydrogenated to alcohols, the dehydrated alcohols to olefins, and the resulting hydrogenated or non-hydrogenated olefins to isoparaffins, with triptane being the isoparaffin that is present in the greatest proportion.

BRIEF DESCRIPTION OF THE DRAWINGS

The present invention will be described in greater detail below with reference to the attached FIG. 1, which represents an embodiment of the invention schematically without limiting the scope of the invention.

FIG. 1 shows the Guerbet reaction steps for the production of 2,3,3-trimethylbutanol from 3,3-dimethyl-1-butanol and methanol, and the hydrodeoxygenation (HDO) reaction steps of the products obtained in the Guerbet reaction, either by direct HDO route or by dehydration deoxygenation followed by hydrogenation, thereby leading to the formation of triptene and triptane. The synthesis reactions of methanol from CO or $CO_2$ (SYN MeOH) are also presented.

DETAILED DESCRIPTION OF THE INVENTION

In particular, the present invention relates to a method for obtaining components containing seven carbons in which the four-carbon chain has three methyl branches, preferably 2,2,3-trimethylbutane (triptane). In addition to triptane, the present invention also encompasses the production of 2,3,3-trimethyl-1-butene (triptene), 2,3,3-trimethylbutanol (triptanol), and 2,3,3-trimethylbutyraldehyde (triptanal).

The invention is characterized in that it employs the coupling of alcohols (Guerbet reaction) in a first step, preferably using 3,3-dimethyl-1-butanol (neohexanol) and methanol (MeOH) as starting compounds. Said reaction is catalyzed by a catalyst that combines a hydrogenating/dehydrogenating function and a basic function, resulting in a product that contains high levels of triptanol.

Thus, the production method described in the present invention involves the reaction of a primary and/or secondary alcohol (or mixture of alcohols) (Guerbet reaction), which takes place through the following steps:

a. Dehydrogenation: hydroxyls dehydrogenate to carbonyls (generating 2 $H_2$), primary alcohols to aldehydes, neohexanol to 3,3-dimethylbutyraldehyde (neohexal), and methanol to formaldehyde;

b. Aldol condensation: the aldol condensation between two carbonyl-containing molecules (aldehyde or ketone), followed by elimination of water, producing the intermediate enone ($\alpha,\beta$-unsaturated acetone), 2(tert-butyl)acrylaldehyde.

c. Hydrogenation: the enone is hydrogenated with the $H_2$ produced from the original hydroxyl groups of the alcohols, resulting in triptanol.

In the described reaction steps, it is also possible to use (i) methanol precursors in order to form methanol in situ, or mixtures of methanol with the precursors thereof; and (ii) corresponding intermediate aldehydes such as neohexal and formaldehyde.

Under Guerbet reaction conditions, triptanol also dehydrogenates triptanal (2,3,3-trimethylbutyraldehyde), resulting in a Guerbet reaction product containing a mixture of triptanol and triptanal.

In a continuous action, triptanol or a mixture of triptanol and triptanal can be converted to triptane and/or triptene through the removal of oxygen by hydrodeoxygenation (HDO).

When done by means of hydrodeoxygenation (HDO), the removal of oxygen from the oxygenated compounds products of the Guerbet reaction is carried out using heterogeneous HDO catalysts. Catalysts usually combine the hydrogenating and acidic function, in which the alcohol is dehydrated and subsequently hydrogenated, or the function of the direct hydrodeoxygenation of the alcohols and carbonyls, both in an $H_2$ atmosphere.

Still in relation to this feature of the invention, the mixture of triptanol with triptanal resulting from the alcohol coupling reaction described herein is sent to the HDO stage, preferably resulting in triptane. Depending on the catalyst and the hydrodeoxygenation conditions, the formations of triptene or triptane are promoted.

As an alternative to HDO, deoxygenation—i.e., the transformation of triptanol and triptanal into triptane and/or triptene—can be achieved by two sequential steps: dehydration of the alcohol with an acid catalyst to triptene, and the final hydrogenation step of triptene to triptane in the presence of a hydrogenating catalyst.

A hydrogenation step may be required prior to dehydration in which triptanal is hydrogenated to triptanol for the purpose of dehydration. However, a hydrodeoxygenation catalyst (HDO) is preferably used which is capable of hydrogenation or carbonyl removal and performing hydrodeoxygenation (HDO) by direct route.

With regard to the Guerbet and HDO reactions, the coupling step and the hydrodeoxygenation (HDO) can occur in the same reactor or in different reactors. These are preferably carried out in different reactors, with recovery of unreacted methanol, neohexanol, and neohexal in the Guerbet reaction step and recycling thereof to the Guerbet reactor.

During the Guerbet reaction step, the coupling reaction of neohexanol with itself may occur in addition to the reaction with methanol, producing heavy-branched alcohol; this is avoided by using higher proportions of methanol or precursors.

Still in relation to the methanol content per reaction, it is noteworthily higher than the stoichiometric—at least 2 mol of methanol per mol of neohexanol.

Furthermore, the methanol/neohexanol ratio is at least 3:1 mol:mol, more preferably in the range of 9:1 mol:mol, the selectivity being greater in the ratio of 12:1 mol of methanol to mol of neohexanol. Higher levels of methanol beyond the 12:1 mol:mol ratio have no beneficial effect, probably due to the dilution of the neohexanol.

Hydrogenolysis of methanol to CO and $2H_2$ also occurs during the Guerbet reaction. Also, a portion of the CO reacts with $H_2O$, the reaction product forming $CO_2$ and more $H_2$.

It was also found that, for the claimed catalysts, methanol can be produced in situ in the Guerbet reaction step from CO and hydrogen, $CO_2$ and hydrogen, or a mixture of the two. Mixtures of CO, $CO_2$, and $H_2$ gases can still be combined with methanol in the reactor feed. More preferably, CO and $CO_2$ and $H_2$ effluent gases from the Guerbet reaction step are fed back to the Guerbet reactor.

In addition to methanol, formaldehyde can also be fed to the reactor, since it is the intermediate of the reaction produced by the dehydrogenation of methanol. However, the use of methanol and/or the combination thereof with synthesis gas (CO and $H_2$) are preferred, since formaldehyde can polymerize, obstructing access to catalyst sites. Under the claimed conditions of the present invention, the chemical equilibrium calculation indicates that the amount of formaldehyde formed is small, and the absence of formaldehyde in the analysis of the product indicates that it reacts rapidly.

The hydrogenolysis reaction of methanol to CO and $H_2$ is endothermic, whereas the synthesis reaction of methanol from CO and $H_2$ is exothermic. Therefore, the combination of methanol with synthesis gas (CO and $H_2$) in the charge imparts an additional advantage to the method, since it reduces the need to supply heat in order to achieve the reaction conditions, making the temperature profile in the reactor nearly isothermal, thereby promoting the alcohol coupling reaction.

Thus, the Guerbet reaction can be fed either by mixtures of CO and $H_2$ or $CO_2$ and $H_2$ or a mixture of the two, or by methanol or a mixture of the gases. The presence of $H_2$ has an effect on the methanol synthesis reaction when the feedstock contains CO (synthesis gas). If $CO_2$ is used as a reagent, higher levels of $H_2$ are required for hydrogenation.

The CO when hydrogenated to methanol requires the consumption of two $H_2$ molecules. Otherwise, three $H_2$ molecules are required in order for $CO_2$ to be hydrogenated to methanol. The alcohol coupling reaction occurs with compounds containing a carbon as reactants, either methanol or mixtures of $H_2$ and CO or $CO_2$ or even formaldehyde, provided that there are adequate conditions for the formation of methanol and, in turn, formaldehyde.

The methanol synthesis reaction can be carried out in a reactor that is different from the Guerbet reactor prior to mixing with neohexanol. Likewise, methanol synthesis can also occur in situ, parallel to the alcohol coupling reaction.

Catalysts used in the coupling of alcohols have a basic function and a hydrogenating/dehydrogenating function. The reaction is thus carried out at temperatures of greater than 150° C., preferably greater than 200° C., more preferably greater than 300° C. Temperatures of greater than 450° C. are unnecessary and lead to increased formation of secondary reactions, although temperatures up to 550° C. can be used. The Guerbet reaction thus takes place at temperatures in the range of 150° C.-550° C., preferably 150° C.-450° C.

It is also noteworthy that the coupling reactions of alcohols develop at pressures of greater than 5 bar, preferably greater than 10 bar, more preferably greater than 20 bar, and less than 100 bar. Pressures of greater than 60 bar lead to smaller gains and are not preferred conditions, although pressures of up to 200 bar can be used. The greater the pressure, the greater the thermodynamic favoring of the alcohol coupling reaction.

Temperature and pressure are correlated, since higher pressures disfavor dehydrogenation, and higher temperatures are necessary in order to maintain the same level of dehydrogenation. Very low pressures result in a need to increase the reaction time, however.

It should therefore be emphasized that the conditions described in this invention are ideal for the coupling of alcohols between neohexanol and methanol, resulting in triptanol and triptanal.

Various forms of contact between the catalyst and the reactants are possible in the present invention. Batch mixed reactors, continuous mixing reactors (CSTR), batch or continuous reactors with homogeneous catalysts or, preferably, continuous reactors with heterogeneous catalysts can be used.

In the present invention, the use of heterogeneous catalysts facilitates the separation of the products from the catalyst. Since the proportions between basic and hydrogenating functions are such that the catalyst deactivation is small, the preferred form of contact between the reactants and the catalyst is through reaction, with the catalyst in a fixed bed with impinged flow. Other continuous reactor setups, such as slurry beds or fluidized beds, are possible, but they do not have advantages over the preferred method of continuous fixed-bed reaction. Furthermore, homogeneous catalysts (basic catalyst) and heterogeneous catalysts (hydrogenation/dehydrogenation catalyst) can be combined.

For a continuous fixed-bed reaction, feed volumes (mixture of neohexanol and methanol) processed per unit time per reactor volume (LHSV) are typically 0.1 to 10 $h^{-1}$. More preferably the LHSV (charge volume per hour per reactor volume) is from 0.5 to 5 $h^{-1}$, more preferably from 0.5 to 2 $h^{-1}$.

Hydrogen is not necessary for the reaction, since it is produced and consumed in the alcohol coupling reaction itself, in the steps of the dehydrogenation and hydrogenation of the enone, respectively.

However, the presence of hydrogen may be desired in order to increase the campaign time and favor triptanol and, to a lesser extent, triptanal, as the product. Without limiting the claims to an understanding of the mechanism of action of hydrogen, the hypothesis is that the presence of hydrogen keeps the catalyst partially reduced, promoting the evaporation and hydrogenation of reactive intermediates, such as enone, which could lead to the formation of coke in the catalyst.

Not counting the hydrogen ($H_2$) required for the synthesis of methanol, when mixtures of CO and/or $CO_2$ are used in the Guerbet reactor with additional $H_2$, the molar ratio of $H_2$ is between 0 and 10 mol $H_2$/mol neohexanol, and preferably between 0 and 5 mol $H_2$/mol neohexanol, more preferably 0 to 2 mol $H_2$/mol neohexanol. Preferably, hydrogen ($H_2$) is not necessary, but it can be used for heating the reactor bed and for activation in order to remove adsorbed $CO_2$ under the conditions in which the Guerbet catalyst is prepared.

The Guerbet reaction produces $H_2O$ as a byproduct. $OH_2O$ can also react with methanol and CO in a water-gas-shift reaction, resulting in more $H_2$ and forming $CO_2$, which is the origin thereof in the effluent gas from the Guerbet reaction. Metals with hydrogenating/dehydrogenating capacity are known to catalyze these reactions. As is known in the prior art, various reactions can occur starting from methanol, the primary ones being methanol to dimethyl ether and methanol to formaldehyde, which can, in turn, react to methyl formate, which decomposes to $CO_2$ and methane or CO and $H_2$.

It is known in the prior art that Copper (Cu) is a catalyst for the hydrogenation of CO and $CO_2$ to methanol, primarily if promoted by ZnO. Other active metals for the reaction include Fe, Ni, Pd, Pt, Rh, and Ru, among others. It was thus found in the present invention that the claimed Guerbet reaction catalysts also have activity for in situ methanol synthesis.

In addition to 3,3-dimethyl-1-butanol (neohexanol), 3,3-dimethyl-1-butanone (neohexal) can be used as a reagent. Neohexal is the intermediate of the alcohol coupling reaction obtained from the dehydrogenation of neohexanol. Neohexal can be formed in a separate reactor prior to contact with methanol. Neohexanol can be dehydrogenated under conditions similar to the alcohol coupling reaction, preferably in lower pressure conditions.

In the event that the neohexanol is dehydrogenated prior to the Guerbet reaction, the same catalyst of the Guerbet reaction with a hydrogenating/dehydrogenating function can be used, but a catalyst with lower basicity, more preferably without basicity, is preferably used. Even more preferably, the catalyst has neither acidity (which could form ethers or dehydrate the alcohol to olefin) nor basicity (which could result in Guerbet alcohols as a result of the condensation of two molecules of neohexanol).

In general, when neohexanol is dehydrogenated prior to the coupling reaction, the preferred conditions are reduced pressure and higher temperatures in order to effect the dehydrogenation.

By comparison, when alcohols are used as reagents, higher pressure conditions are preferable for alcohol coupling (Guerbet reaction) and the formation of Guerbet alcohols, this being taught in the method described in the present invention.

Preferably, unreacted neohexal and neohexanol are separated from the product after the alcohol coupling reaction and recycled together or separately. Distillation is one of the primary ways of separating neohexal and neohexanol from alcohol coupling reaction products. If a previous reactor is used for the neohexanol dehydrogenation step, the unreacted neohexanol is fed to this reactor, and the neohexal is fed directly to the alcohol coupling reactor.

In addition to methanol, it is possible in the alcohol coupling reaction described above to use formaldehyde, which is an intermediate in the reaction that is obtained from the dehydrogenation of methanol. Formaldehyde is obtained industrially from the dehydrogenation of methanol and, more commonly, from the oxidative dehydrogenation of methanol.

The conditions for obtaining formaldehyde typically involve higher temperatures and lower pressures than those employed in the alcohol coupling reaction of the present invention. Furthermore, the consumption of $H_2$ produced in the dehydrogenation by reaction with oxygen (oxidative dehydrogenation) usually favors the production of formaldehyde. Under typical conditions of the invention, the expected amount of formaldehyde is thus reduced.

Despite the ease of obtaining formaldehyde, the use of methanol is preferred, since formaldehyde is quite reactive and tends to polymerize in aqueous solutions, forming poly(oxymethylene) glycols. This reactivity leads to the formation of polymers that can deactivate the Guerbet catalyst or form deposits in process equipment (furnaces, heat exchangers).

A portion of the methanol is converted into synthesis gas in the Guerbet reaction step and, under the conditions of the invention, the gas phase is preferably fed back to the reactor using a recycle gas compressor. Preferably, a portion of the gas can be purged and the $H_2$ fed in order to maintain the ratio between $H_2$ and CO at 2 mol:1 mol. More preferably, there is a recycle compressor for recompressing the product gas and returning it to the reaction. There is also preferably injection of methanol and/or $H_2$ and gas purging, if necessary, in order to maintain continuous reactor operating conditions with the desired excess of methanol and/or methanol precursors.

Regarding the catalysts used in the alcohol coupling reaction, it should be noted that they can be selected from among: homogeneous catalysts, salts, hydroxides, and alkoxides, preferably associated with hydrogenating/dehydrogenating catalysis functions, homogeneous or not. Preferably, heterogeneous catalysts are used; more preferably, a metal with hydrogenating/dehydrogenating function is used on a basic support, or on a support containing a basic component.

The basic supports or components can be selected from among oxides, hydroxides, phosphates, carbonates, carbides of elements of group IA and IIA, alkali metals, and/or alkaline earth metals such as K, Na, Ca, Cs, Sr, Ba, and Rb. In addition, a basic component or a mixture of components, such as mixed oxides, are used.

Alternatively, supports such as aluminas, silicas, or zeolites doped with basic components such as K, Ca, or Mg, usually as oxides ($K_2O$, CaO), can be used.

Furthermore, with regard to the supports themselves, these can be basic, such as alkaline earth metal oxides, such as MgO, CaO, SrO, and BaO, and rare earth oxides such as CeO, $La_2O_3$, $Sm_2O_3$. Besides $Al_2O_3$, other oxides that lend themselves to the present invention as a support are $ZrO_2$, $Y_2O_3$, ZnO, $TiO_2$, $MoO_3$, and $ThO_2$, which can also be dual-component oxides such as $ZnO$—$Al_2O_3$, $MgO$—$TiO_2$. In general, alkali metal ions are used which are supported on alumina, silica, and the abovementioned oxides, primarily alkaline earth metal oxides. The ions are primarily employed as oxides but can be non-oxides such as KF and KCl supported on alumina, and lanthanide imides and nitrides.

Basic zeolites can also be used as basic supports and may have alkaline ions due to ion exchange, such as Na—X, Cs—X, or they may have added alkali, as in the case of $CS_2O/CS$—X. Other possibilities are the above-mentioned zeolites exchanged with basic metals, transition metals, rare earths, higher-valence oxides.

Other basic supports are basic clays and clay minerals such as limestone, dolomite, magnesite, chrysolite, sepiolite, olivine, and hydrotalcite.

With regard to hydrotalcites, they are lamellar double hydroxides, where a divalent cation (such as Mg, Mn, Fe, Co, Ni, Cu, Zn, Ga) is combined with a trivalent metal (Al, Cr, Mn, Fe, Co, Ni, La), plus a compensation anion between the lamellae. Hydrotalcite can also be doped with additional metal. Hydrotalcites can be calcined or non-calcined, resulting in mixed oxides and spinels, depending on the condition.

Another version of the present invention are the hydroxyapatites, used as basic catalysts. Perovskites, beta-aluminas, hydroxides, and metallic carbonates in general can also be used. Other supports are metal or supported nitrides, nitrates, sulfides, sulfates, carbides, phosphates and fluorides; activated and impregnated carbons; anion exchange resins; organic bases supported on microporous or mesoporous metal oxides; in general, solid or supported alkalis and alkaline earth metals or basic organometallics. However, the invention is not limited to the nature of the component that confers the basic function used in the Guerbet catalyst, it being possible to fulfill the same basic function in the reaction with different basic compounds.

On the same topic, another support, alumina, especially gamma-alumina, has become an alternative due to the fact that, despite its unwanted intrinsic acidity, it has a good surface area and pore distribution, in addition to having adequate properties for being doped with alkali metals and/or alkaline earth metals such as K, Na, Ca, Cs, or Rb.

In addition to the basic components used in the catalyst, nitrogen compounds can be used in solution, in the charge, under the reaction conditions. Nitrogen compounds are selected from among but not limited to amines, ammonia, basic nitrogens. The component used is preferably ammonia, or any nitrogenous compound that minimizes the parallel reactions involving the dehydration of alcohols and the formation of ethers. Without limiting the present invention to a hypothesis concerning the inhibition of the dehydration and etherification reactions, it is assumed that nitrogenates and ammonia compete with the reactants for remaining acidic sites, inhibiting the undesired side reactions of dehydration and etherification. Ammonia or nitrogen can be added to the feed, resulting in a nitrogen content of 0 to 5000 ppm.

The hydrogenating/dehydrogenating function of the catalyst used in the alcohol coupling reaction (Guerbet reaction) can be transition metals, specifically from group VB, VIB, VIIIB, IB, such as V, Cr, Mo, W, Fe, Ru, Rh, Re, Co, Ni, Cu, Ag, Sn, Pb, Zn, Mn, Pt, and Pd, alone or in combination. Preferably, the metals are Cu and/or Ni. Metals may or may not be promoted by other metals such as Zn. Metals can be present as oxides, hydroxides, salts, or reduced. The aforementioned metals can still be present as a homogeneous catalyst system, supported or unsupported.

It is also possible to use a mixture of different catalysts, including a basic solid and a hydrogenating catalyst. More preferably, the basic and hydrogenating functions are combined in the same catalyst. The basic function may also be present as a homogeneous or heterogeneous catalyst, and the hydrogenating/dehydrogenating function may likewise be present in a homogeneous or heterogeneous form, it being possible to have a homogeneous basic phase with a supported hydrogenating catalyst or a heterogeneous basic phase and a homogeneous hydrogenating function. However, the preferred catalyst combines the two functions in the same heterogeneous catalyst.

In a particular aspect of the invention, the catalyst is Cu deposited on potassium-doped gamma-alumina. Said catalyst is prepared so as to preferably contain Cu(I) copper species, with more activity for the alcohol coupling reaction than fully reduced copper, Cu(0). Cu(I) can be prepared using precursors such as $CuCl_2$, which reduces CuCl when reacted with KOH on the catalyst surface. The preferred method of catalyst preparation is to impregnate ethanolic $CuCl_2$ solution in alumina, and after calcination, to impregnate KOH solution, followed by final calcination.

Another related aspect relates to the fact that Cu catalysts in ZnO and $Al_2O_3$ mixtures are effective, primarily for the hydrogenation of CO (and $CO_2$) to methanol. To wit, ZnO combined with K or another basic component potentiates the formation of Cu(I) at the expense of divalent or reduced copper.

In order for the reaction described in this method to operate under optimal conditions, the Cu content in the catalyst is at least 1% by weight, preferably greater than 2% by weight and less than 10% by weight, and preferably in the range of 5% by weight. Likewise, the KOH content in the alumina is from 5% to 30% by weight, preferably greater than 10% by weight, and in a preferred aspect, equal to 20% by weight. Contents of greater than 30% by weight lead to pore occlusion and an exacerbated decrease in the catalyst surface area.

In addition to the preferential use of Cu, another metal can be used together with Cu to potentiate the dehydrogenation and methanol activation reactions, including but not limited to Pd, Pt, Fe.

It should also be noted that the Guerbet reactions are thermodynamically limited. One way to promote an increase in the conversion of neohexanol is to work under conditions which are such that part of the triptanol is converted into triptanal, thereby increasing the conversion of neohexanol. This can be achieved with higher temperatures, more active catalyst, longer residence time of the reactants in the reactor (shorter LHSV), among other procedures that are known in the art.

Unreacted neohexanol and neohexal can be separated from the reaction products and fed back to the Guerbet reaction step. It is also possible to partially hydrogenate and dehydrate them before separation. Since triptanol is an alcohol with a more branched molecule, it can be more easily dehydrated than neohexanol. Furthermore, it is possible to promote the conversion of triptanol and triptanal to triptene and triptane without substantially converting neohexanol to neohexene and corresponding paraffins, because substantial differences exist between the boiling point of triptane and neohexanol, which facilitates separation.

In addition to triptanol and the dehydrogenation product thereof, triptanal, other byproducts can also be formed in the reaction, such as methyl ether (dimethyl ether), triptanol methyl ester, or neohexanol, and ethers such as triptanol methyl ether or neohexanol, and dehydration products of neohexanol and triptanol.

Part of these byproducts—the ethers and esters—can be reused through the hydrolysis reaction. The hydrolysis is carried out by reacting ether with water in an acid catalyst, such as an acidic ion exchange resin or acid catalysts that are known in the art. For hydrolysis, it is necessary to feed water to the hydrolysis reactor at least in stoichiometric proportions.

Alternatively, direct recycling of the ethers can be performed, or the remaining ethers can be mixed and reacted with alcohols in the Guerbet reactor. In this particular case, it may be of interest to feed $H_2O$ to the reaction charge, although the Guerbet reaction itself produces water. Optionally, water can be fed to the Guerbet reactor charge also in order to reduce the etherification and dehydration reactions.

Since, in ideal reaction conditions, an excess of methanol is used in relation to the stoichiometric value, it is important to separate the same for later reuse in the reaction described in the present invention. It should be noted that the presence of methanol in the hydrodeoxygenation step can lead to the hydrogenation thereof to methane, resulting in unnecessary consumption of hydrogen. Methanol can be recovered either through distillation or extraction.

Still in relation to the recovery of methanol, it can be performed using the liquid-liquid extraction method, since triptanol and triptanal are less soluble in water, so the heavy alcohols remain in the organic phase while the methanol passes on to the aqueous phase. Typical amounts of water relative to the organic phase content are 0.1 to 5 times, preferably 0.5 to 2 times the volume of the organic phase, more preferably a 0.1 to 1 ratio of aqueous phase to organic phase by volume. Extraction can occur in only one contact equilibrium stage, or it can preferably occur in a counter-stream in more than one separation stage. The water can be added later to the Guerbet reactor, or it can be present in the Guerbet reactor charge.

Methanol can be reallocated in the form of an aqueous solution to the Guerbet reaction, or it can be separated from the water prior to the reaction by distillation. The aqueous methanol solution can also be mixed with dimethyl ether and sent to a hydrolysis reactor to increase methanol recovery, with a decrease in the water content that is consumed in the reaction.

The separation of alcohols and the hydrolysis of ethers can still be combined in order to preferably recycle the unreacted alcohols by using catalytic distillation with acid catalyst in distillation portions.

Preferably, the methanol is removed after the alcohol coupling reaction (Guerbet) and recycled to the initial step of said reaction. The reaction product gas is likewise returned to the initial reaction step. Triptane is thus obtained in two reactors in sequence, the first with the Guerbet reaction, and the second with the conversion of triptanol and triptanal to triptane through the hydrodeoxygenation reaction (HDO).

It is also noteworthy that the hydrodeoxygenation reaction (HDO) can be a combination of dehydration and hydrogenation reactions, in which case the acid function and the hydrogenating function are located in the same catalyst. Alternatively, a direct HDO catalyst is used. For the hydrodeoxygenation (HDO) step, the presence of hydrogen is necessary for the conversion of triptanal to triptanol, as well as for the hydrogenation of triptene to triptane.

Without the intermediate removal of excess methanol after the Guerbet reaction, it could be converted either into dimethyl ether (by the acidic function in the catalyst) or hydrogenated to methane, with both reactions also generating water. Likewise, the CO and $CO_2$ effluent gases from the first reaction can also be converted to methane in the HDO step.

Thus, the gas containing $H_2$, CO, and $CO_2$ from the alcohol coupling reaction (Guerbet reaction) is preferably returned to the Guerbet reaction, with $H_2$ being added to maintain a desired molar ratio of methanol and methanol precursors. Also, it may be necessary to purge part of the gas to avoid accumulation of inerts (light hydrocarbons, primarily methane) formed in the reaction. The methane and light gases formed in the reaction can be sent to a synthesis gas/methanol production unit.

Although it is possible to use two different catalyst beds in the same reactor, one for the alcohol coupling reaction (Guerbet reaction) and another for the hydrodeoxygenation reaction (HDO), it is preferable to have different reactors for each stage. In a preferred aspect of the present invention, unreacted methanol and product gas are separated after the alcohol coupling step and prior to the hydrodeoxygenation (HDO) reaction step.

Still under the claimed conditions of the present invention, the conversion of neohexanol is greater than 75%, more commonly greater than 90%. In these terms, neohexanol and neohexal can be separated through distillation reactions and returned to the alcohol coupling reactor or Guerbet reactor.

In another aspect of the invention, once the mixture of triptanol and triptanal is obtained from the Guerbet reactor, such components can be used for purposes other than the production of triptane and/or triptene, with the obtaining of triptanol and triptanal being one of the embodiments of the present invention. Triptanol can be further dehydrogenated in order to increase the yield of triptanone.

For the subsequent hydrodeoxygenation (HDO) reaction, commercially available catalysts such as hydrotreating catalysts, Mo or W sulfides are commonly used, promoted by Ni or Co, and supported on solids such as alumina, silicas, silica-aluminas, zeolites, hydrotalcites, mixed oxides, spinels, MgO, $TiO_2$, ZnO, $CeO_2$, phosphates, sulfonic resins, $ZrO_2$, sulfated Zr, carbon, activated carbon, inter alia. More commonly, Mo sulfides are used which are promoted by Ni and supported on gamma-alumina.

Catalysts are present at typical levels of 10 to 20% by weight, typically 15% by weight Mo, plus 5% Ni (as $MoO_3$ and NiO) supported on $Al_2O_3$. It is necessary to carry out sulfidation before using the catalyst, or to use a pre-sulfide catalyst, which is also commercially available. With regard to the use of sulfide catalysts, it may be necessary to dope the charge with sulfur compounds, either continuously or intermittently, in order to maintain the sulfide catalyst.

In addition to sulfide catalysts, completely or partially reduced metals such as Pt, Pd, Ru, Ni, Cu, Mo, W, Co, Ir, Rh, Au, Ce, Fe, Mn, Ga, Pb, Bi can be used in subsequent hydrodeoxygenation (HDO) reactions. Of these, metals that are supported on the supports described above are preferably used. In addition to reduced metals, other catalysts such as oxides, phosphates, carbides, and nitrides are known, some examples being $MoO_3$, NiP, $MoC_2$, and $CoNx$.

Among the sulfide catalysts used in subsequent hydrodeoxygenation (HDO) reactions, $MoO_3$, in the presence of $H_2$, has the ability to remove carbonyl oxygen and alcohols, resulting in alpha-olefin. In addition to $MoO_3$, Mo carbides and nitrides can affect the direct HDO of alcohols and carbonyls. Due to a lack of oxygen, the mechanism of action of the catalysts is created by $H_2$ in a reverse Mars-Van Krevelen mechanism of the activation of the C—O bond. In addition to $MoO_3$, the same mechanism also occurs with $RuO_2$, $IrO_2$, PdO, and $Rh_2O_3$. Other catalysts with lower activity are $SnO_2$, ZnO, $VO_2$, $TiO_2$, and $CeO_2$, in addition to CuO, $Ag_2O$, and $Au_2O_3$.

Some noteworthy supports that are oxophilic, meaning that they have an affinity for oxygen, which can promote the hydrodeoxygenation reaction (HDO), include carbon, alumina, $TiO_2$, and $ZrO_2$.

Acidity is also required for oxygenate activation, including the dehydration of alcohols, which may promote the hydrodeoxygenation (HDO) reaction through a dehydration-plus-hydrogenation mechanism, as is the case with alumina-supported catalysts. Furthermore, acidity of some supports may favor the dispersion of the metallic function from the hydrodeoxygenation (HDO) reaction. However, the direct mechanism of hydrodeoxygenation is preferred.

One class of commercially available catalysts for the hydrodeoxygenation (HDO) reaction are the hydrotreating (HDT) catalysts of petroleum fractions. They are generally Mo or W sulfides that are promoted by Co or Ni, preferably Ni, when greater hydrogenation of triptene to triptane is desired. In sulfide catalysts, it may be necessary to add sulfur to the feedstock, either continuously or intermittently, in order to maintain the active phase sulfide.

Typical pressure conditions ranging from 5 to 100 bar, preferably 10 to 50 bar, more preferably 20 to 40 bar are sufficient to obtain triptane from the mixture of triptanol and triptanal. Typical temperatures range from 200 to 400° C., preferably from 200 to 350° C., more preferably from 250 to 325° C. Lower temperatures reduce the efficiency of the hydrodeoxygenation step, and higher temperatures can lead to isomerization of the seven-carbon chain, resulting in lower-octane hydrocarbons.

The charge for the hydrodeoxygenation reaction (HDO) can contain neohexanol and neohexal. However, the neohexanol and neohexal are preferably removed prior to the hydrodeoxygenation (HDO) reaction. Under milder conditions, neohexanol is more difficult to hydrodeoxygenate than triptanol, which is why it is possible to recover most of the neohexanol after the hydrodeoxygenation (HDO) reaction under low stringency conditions.

The present invention therefore relates to the transformation of the alcohol coupling product, namely triptanal and triptanol into triptane and/or triptene, without parallel reactions such as the formation of ethers, demethylation (cracking), decarbonylation, or isomerization of the seven-carbon chain.

Dehydration and hydrogenation reactions may be necessary in order to obtain triptane and triptene from triptanol and triptanal. Hydrogenation converts triptanal to triptanol, which, in turn, is dehydrated to triptene and then hydrogenated to triptane. It is also possible not to hydrogenate the triptene, which could be the final product.

The neohexanol used in the present invention is obtained using several methods, including: (i) hydration of the neohexene; (ii) the reaction of isobutene with ethylene in sulfuric acid, followed by hydrolysis; (iii) the reaction of tert-butyl alcohol with ethene in sulfuric acid; (iv) the reaction of isobutene with ethanol in sulfuric acid; (v) the metathesis of isooctene with ethylene, resulting in neohexene (vi) from the combination of the isobutene dimerization reactions, isomerization of the position of the olefin in the C8 chain, and metathesis. Furthermore, neohexal can be produced directly by any means known in the art for use as a reagent in the present invention.

It is noteworthy that the heterogeneous catalyst is important for the method, exhibiting both basic and hydrogenating/dehydrogenating functions. It should also be noted that various heterogeneous or homogeneous catalysts are capable of catalyzing the reaction of 3,3-dimethyl-1-butanol or neohexal with methanol or a precursor thereof, resulting in seven-carbon components, more preferably triptane.

In this regard, the present invention relates to a method for the production of seven-carbon compounds with three methyl branches that involves the coupling of alcohols (Guerbet reaction, steps a, b, and c) followed by a hydrodeoxygenation (HDO) reaction, as described in the following steps:

a. Coupling: steps of (i) Dehydrogenation: The hydroxyl of the alcohols is dehydrogenated, forming carbonyls. Such a reaction produces two molecules of hydrogen ($H_2$). In this step, the primary alcohols are transformed into aldehydes; in particular, if 3,3-dimethyl-1-butanol (neohexanol) is used, this is transformed into 3,3-dimethylbutyraldehyde (neohexal), and the methanol is transformed into formaldehyde; (ii) Aldol condensation: In a second step, the aldol condensation is carried out between the two carbonyl-containing aldehyde molecules resulting from step (a), followed by the elimination of water. The result of this step produces an intermediate enone ($\alpha,\beta$-unsaturated acetone); finally, (iii) Hydrogenation: The enone obtained in step (b) is hydrogenated with the hydrogen ($H_2$) produced in step (a), resulting in triptanal and, predominantly, in triptanol.

b. Deoxygenation: The alcohol and aldehydes resulting from step (a) undergo an oxygen removal step, resulting in the production of a seven-carbon hydrocarbon with three methyl branches, either by dehydration reaction and subsequent hydrogenation, or by hydrodeoxygenation with $H_2$, with said alcohol being transformed into triptane and triptene. 1

That said, generically speaking, it is the object of the present invention to provide a method for obtaining seven-carbon compounds with three methyl branches through the reaction between a six-carbon oxygenated compound and an oxygenated compound containing one carbon.

In this inventive aspect, it should be noted that triptane is obtained through two reactions in sequence, including the first alcohol coupling reaction (Guerbet reaction), which includes dehydrogenation, aldol condensation, and hydrogenation, and the second reaction, in which triptanal and triptanol are converted to triptane, namely the hydrodeoxygenation (HDO) reaction.

In a first aspect of the present invention, it should be noted that the six-carbon oxygenated compound is selected from among 3,3-dimethyl-1-butanol and 3,3-dimethylbutanal or a mixture of the two.

In a second aspect, the oxygenated compound containing a carbon is selected from among methanol, formaldehyde, paraformaldehyde, and methanol precursor mixtures, such as the mixture of $H_2$ with CO, $CO_2$, or a mixture thereof.

A third aspect relates to the Guerbet catalyst for the reaction between the oxygenated compounds, which is heterogeneous in that it combines the hydrogenating/dehydrogenating function with the basic function.

In a fourth differentiated aspect, the dehydrogenating/hydrogenating function of the catalyst is selected from among transition metals from the groups VB, VIB, VIIIB, IB, primarily Cu, Ni, V, Cr, Mo, W, Fe, Ru, Co, Pt, and Pd, which are present in the catalyst in the form of oxides, carbonates, halides, phosphates, carbides, nitrides, or even as reduced metals.

In a fifth aspect, the basic function of the catalyst is to be selected from among basic compounds, alkali metals, and alkaline earth metals from the groups IA and IIA in the form of oxides, hydroxides, phosphates, carbonates that are supported or not supported on heterogeneous supports such as aluminas, hydrotalcites, zeolites, silicas, silica-aluminas, activated carbon, mixed oxides, spinels, or basic clays such as limestone, dolomite, magnesite, sepiolite, olivine, in addition to anion exchange resins, metallic oxides such as ZnO, and basic organometallics.

In a sixth related aspect, it is worth noting that the present method still presents byproducts to be selected from among 2,3,3-trimethyl-1-butanol or a mixture of 2,3,3-trimethyl-1-butanol and 2,3,3-trimethylbutyraldehyde.

With regard to another added aspect, the Guerbet catalyst is Cu supported on K-doped alumina and operates at a temperature in the range of 150 to 550° C., preferably from 200 to 500° C., more preferably from 300 to 450° C. Still in relation to said catalyst, it should be noted that it operates at a space velocity (LHSV) of 0.1 to 10 $h^{-1}$, preferably 0.5 to 5 $h^{-1}$, more preferably 0.5 to 2 $h^{-1}$.

Still in relation to the aspect of the operation of the Cu catalyst supported on K-doped alumina, the optimal operating pressure varies in the range of 5 to 200 bar, preferably from 10 to 100 bar, more preferably 20 to 60 bar, and the volumetric ratio of $H_2$ per oxygenated compound containing six carbons is 0 to 10 mol $H_2$/mol, preferably 0 to 5 mol $H_2$/mol, and more preferably 0 to 2 mol $H_2$/mol.

Still with regard to the same inventive aspect, the molar ratio of the oxygenated compound containing one carbon to the oxygenated compound containing six carbons is from 1 to 20 mol:mol, preferably from 2 to 16 mol:mol, more preferably from 6 to 9 mol of oxygenate containing one carbon to mole of oxygenate containing six carbons.

Furthermore, the molar ratio of $H_2$ per oxygenated compound containing one carbon is greater than or equal to 2 mol:mol; when the compound with one carbon is CO and when the compound with one carbon is $CO_2$, the molar ratio of hydrogen ($H_2$) is greater than or equal to 3 mol:mol $CO_2$.

In a particular inventive aspect, the Guerbet reactor can operate without adding hydrogen when the oxygenated carbon compound is methanol.

In a preferred aspect of the invention, the effluent from the Guerbet reaction step undergoes removal of excess methanol in the product prior to the deoxygenation step, which is preferably hydrodeoxygenation.

One differentiated aspect relates to the fact that, after deoxygenation, seven-carbon compounds with three methyl branches are obtained.

In one differentiated aspect, the deoxygenation is carried out by a hydrodeoxygenation catalyst (HDO) in the presence of hydrogen ($H_2$).

In another differentiated aspect, deoxygenation is carried out by means of a combined dehydration and hydrogenation reaction, and the catalysts used are partially reduced metals such as Pt, Pd, Ru, Ni, Cu, Mo, W, Co, Ir, Rh, Au, Ce, Fe, Mn, Ga, Pb, and Bi, alone or in mixtures, supported on solids such as alumina, silicas, silica-aluminas, zeolites, hydrotalcites, mixed oxides, spinels, MgO, $TiO_2$, ZnO, $CeO_2$, phosphates, sulfonic resins, $ZrO_2$, sulfated Zr, carbon, and activated carbon, the support being preferably oxophilic, as is the case with alumina, $TiO_2$, and $ZrO_2$.

In one differentiated aspect, the compound obtained in HDO with seven carbons and three methyl branches is 2,2,3-trimethylbutane or a mixture of 2,2,3-trimethylbutane and 2,3,3-trimethyl-1-butene.

In yet another inventive aspect, a hydrotreatment catalyst is used in the hydrodeoxygenation step with sulfides of Mo or W, promoted by Ni or Co, and supported on solids such as alumina, silicas, silica-aluminas, zeolites, hydrotalcites, oxides mixed, spinels, MgO, $TiO_2$, ZnO, $CeO_2$, phosphates, sulfonic resins, $ZrO_2$, sulfated Zr, carbon, and activated carbon.

Still in this same aspect, the hydrodeoxygenation catalyst (HDO) is a partially reduced metal oxide that is supported in a porous solid such as M003, and other metals such as $RuO_2$, $IrO_2$, PdO, $Rh_2O_3$, $SnO_2$, ZnO, $VO_2$, $TiO_2$, $CeO_2$, CuO, $Ag_2O$, and $Au_2O_3$.

Therefore, the present invention can be described on the basis of the following examples, which illustrate some particular embodiments of the present invention and should not be interpreted as limiting the same. Other interpretations of the nature and mechanism of obtaining the components claimed in the present invention do not change the novelty thereof.

EXAMPLES

Example 1: Catalyst Test

The catalysts were tested at 350° C. on a bench scale, continuous reactor, 10 mL catalyst bed, after activation for 4 h in an $H_2$ atmosphere at 400° C. The charge consisted of a mixture of neohexanol and methanol in a 1:3 molar ratio, pressure of 30 bar, and the volume fed per unit of time per reactor volume, or space velocity (LHSV), was 1 $h^{-1}$, and the ratio of $H_2$/charge was 6 mol $H_2$/mol of neohexanol.

The commercial catalyst of CoO (5% by weight)+M003 (15% by weight) in hydrotalcite (30% by weight MgO) showed activity for the unwanted dehydration of neohexanol to neohexene and formation of the neohexanol methyl ether. Ni catalyst (20% by weight) in MgO showed significant hydrogenolysis capacity of both methanol and neohexanol, producing methane, which is not desired in the present invention.

Example 2. Copper Catalysts on Basic Support

A mass of 100 g of extruded alumina ¹⁄₁₆ in was impregnated with a solution of $CuCl_2.2H_2O$ in a volume of ethanol corresponding to the pore volume of the alumina in order to obtain 5 g of Cu. The alumina containing Cu was dried for 24 h and calcined at 420° C. for 4 h, yielding the Cu/Al intermediate.

Various catalysts were obtained by adding basic solutions to the intermediate. Sodium, magnesium, calcium, and potassium hydroxides were tested in proportions of 5, 10, 20, and 30 g of metal per g of alumina, and the catalysts were subsequently calcined at 420° C. for 4 h.

Potassium-containing catalysts, specifically containing 20 g K/100 g original $Al_2O_3$, exhibited greater conversion and selectivity for the alcohol coupling reaction (Guerbet reaction). Contents of greater than 20 g K/100 g $Al_2O_3$ reduced the mechanical strength of the catalyst. A content of 5% Cu was sufficient for the dehydrogenation reaction step.

When another copper salt was used—the nitrate $Cu(NO_3)_2$ instead of $CuCl_2$—the catalyst proved to be substantially less active. Without limiting the invention to a hypothesis regarding the functioning of the reaction, Cu(I) is more active for dehydrogenation than Cu(0), obtained primarily with the nitrate salt.

Example 3. Tests in a Guerbet Reaction Bench Reactor

Alumina-supported catalyst was used, with 5 g of Cu (from $CuCl_2$) and 20 g of K (from KOH) being added to the 100 g base prepared as described in Example 2.

The catalyst was activated with a temperature of 400° C., and a pressure of 30 bar of $H_2$ for 4 h. The charge had a methanol to neohexanol ratio of 6:1. Test temperatures ranged from 350 to 450° C., the pressure from 10 to 60 bar, the $H_2$/neohexanol ratio from zero to 10 mol/mol, and the LHSV from 0.5 to 2 $h^{-1}$. The temperature of 350° C. proved to be insufficient, whereas the temperature was excessive at 450° C., increasing the formation of light components.

Disregarding the unreacted methanol and dimethyl ether formed, the mixture of products obtained in the tests yielded C7 components, primarily triptanol plus triptanal, in the amount of 74.5% by weight, C6 components (primarily neohexanol and neohexal), in the amount of 23.3% by weight, in addition to light components (1.3%, including triptene and triptane) and heavy components (1%), as products.

Example 4. Bench Reactor Tests for the Hydrodeoxydenation (HDO) of the Guerbet Reaction Product A commercial pre-sulfide NiMo catalyst was activated in an $H_2$ atmosphere at 30 bar.

The product of example 3 was used as the charge.

An LHSV of 2 $h^{-1}$, temperatures from 280 to 400° C., pressure of 30 bar, and an $H_2$/charge ratio of 300 mL $H_2$/mL charge—which would be about 2 mol $H_2$/mol of triptanol if the charge were 100% triptanol—were maintained. The products are primarily C7 carbon charges, in addition to the C6 carbons from the C6 oxygen compounds of the charge. During deoxygenation isomerization also occurred, forming some C7 hydrocarbons other than triptane+triptene. The table shows the result of the test run sequence.

| Temperature (° C.) | Triptanol conversion | Isomerization selectivity |
| --- | --- | --- |
| 320 | 93.68% | 12% |
| 280 | 32.75% | 8% |
| 340 | 87.99% | 12% |
| 380 | 100.00% | 34% |
| 350 | 99.15% | 14% |
| 400 | 100.00% | 39% |
| 360 | 97.42% | 19% |
| 360 | 100.00% | 17% |

Conversion is defined as the amount of triptanol (+triptanal) in the product divided by the amount in the charge. Isomerization selectivity is defined by the amount of C7 hydrocarbons other than triptane and triptene for the total C7 hydrocarbons.

In practice, minimum isomerization with total conversion is desired, which is achieved at temperatures in the range of 320° C. but not higher than 380° C.

Example 5. Tests in Bench Reactor with Higher Methanol Contents in the Alcohol Coupling Reaction (Guerbet Reaction)

Increasing the methanol content in the charge that feeds the reactor 3 mol of methanol to 1 mol of neohexane, 6 mol of methanol to 1 mol of neohexane, and 9 mol of methanol to 1 mol of neohexane increased the conversion and selectivity for triptanol and triptanone. The gain in selectivity and conversion of the 12:1 molar ratio was small.

Example 6. Test in Pilot Reactor 100 mL of the catalyst from example 3 were added to a downflow pilot reactor. The catalyst was preactivated with $H_2$ at 30 m L/min at operating pressure for 4 h at a pressure of 32 bar and temperature of 400° C.

A 9:1 molar charge of methanol to neohexanol was fed, which results from the mixture of 750 ml of methanol with 250 ml of neohexanol, with methanol constituting almost 74% by weight of the charge. The LHSV was 1.0 $h^{-1}$, with 1.666 mL of charge/min being fed. No $H_2$ feed was maintained during the alcohol coupling reaction (Guerbet reaction).

Mass flowmeters showed that 59.8% of the product was in the vapor phase, while 40.2% was in the liquid phase.

Analysis of the product gas showed 66.3 mol % of $H_2$, 11.3% of $CO_2$, 16.4% of CO, 4.5% of methane and other hydrocarbons (totaling 5.6% of light hydrocarbons), in addition to $N_2$ and $O_2$ (contaminants).

The analysis of the liquid product showed 2.6% DME (dimethyl ether), 11.26% methanol, 7% light hydrocarbons (including 2% triptene+triptane), 7.7% neohexal, 2.3% neohexanol, 24.5% triptanal, 36.3% triptanol, 1.0% triptanol methyl ester, and 2.25% other heavier oxygenates, with a total of 63.8% C7 compounds with triptylic branching. Removing the (dimethyl-ether) DME and methanol, neohexal and neohexanol that can be reused, the yield of triptane precursor products reached 84% in the bench test.

The result shows that most of the neohexanol converted to triptanol (and triptanone), while a significant portion of the methanol underwent the inverse hydrogenation reaction, shift reaction with water, forming synthesis gas, $CO_2$ and, to a lesser degree, methane.

Example 7. Test with Methanol Precursor Gas Stream

Test with neohexanol plus synthesis gas stream (2 molar $H_2$:1 molar CO) showed that the desired alcohol coupling reaction (Guerbet reactions) occurred similarly as in the presence of methanol in the feed.

Example 8. Methanol Separation

The addition of 50 mL of water to 50 mL of Guerbet reaction product resulted in 2 phases—68 mL of the aqueous phase and 32 mL of the organic phase. More than 90% of the methanol present in the reaction product passed into the aqueous phase.

Example 9. Test with MeOH Precursor Gas Stream

The test conducted using a mixture of $CO_2$ and $H_2$ in the Guerbet catalyst used in Example 3, with a molar ratio of 4 $CO_2$:1 $H_2$, at 400° C. and 30 bar pressure indicated methanol in the reaction product. The example shows that even $CO_2$ and $H_2$ can be used in the Guerbet reaction.

Thus, as can be seen from the above examples, the method for obtaining triptane from the alcohol coupling reaction (Guerbet reaction) according to the present invention can be carried out on the basis of the conversion of triptanol and triptanal to triptene and triptane.

Those skilled in the art readily understand that the numerous variations which fall within the scope of the present invention are permitted without departing from the inventive scope disclosed herein, for which reason it is emphasized that the present invention is not limited to the above particular embodiments described.

The invention claimed is:

1. A method to obtain seven-carbon compounds with three methyl branches, wherein the method comprises:
    coupling a six-carbon oxygen compound with two methyl branches by a reaction with a one-carbon oxygen compound, resulting in a seven-carbon oxygen compound with three methyl branches; and
    deoxygenating the seven-carbon oxygen compound with three methyl branches resulting in a seven-carbon hydrocarbon with three methyl branches;
    wherein the catalyst of the reaction between the oxygenated compounds is heterogeneous, combining a hydrogenating/dehydrogenating function with a basic function, wherein a majority of the resulting seven-carbon hydrocarbons with three methyl branches are triptane.

2. The method as set forth in claim 1, wherein the compounds used in coupling are an oxygenated compound containing six carbons and an oxygenated compound containing one carbon.

3. The method as set forth in claim 1, characterized in that the six-carbon oxygenated compound used in coupling is selected from among 3,3-dimethyl-1-butanol and 3,3-dimethylbutanal or a mixture of the two.

4. The method as set forth in claim 1, wherein the oxygenated compound containing a carbon used in coupling is selected from among methanol, formaldehyde, paraformaldehyde, or mixtures of $H_2$ with CO, $CO_2$, or a mixture thereof.

5. The method as set forth in claim 1, wherein coupling results in byproducts to be selected from among 2,3,3-trimethyl-1-butanol or a mixture of 2,3,3-trimethyl-1-butanol and 2,3,3-trimethylbutyraldehyde.

6. The method as set forth in claim 1, wherein there is no addition of hydrogen in during coupling when the oxygenated carbon compound used is methanol.

7. The method as set forth in claim 1, wherein deoxygenating comprises dehydration and subsequent hydrogenation of the seven-carbon oxygen compound with three methyl branches.

8. The method as set forth in claim 1, wherein deoxygenating is carried out by a hydrodeoxygenation catalyst (HDO) in the presence of hydrogen ($H_2$).

9. The method as set forth in claim 1, wherein the compound with seven carbons with three methyl branches is selected from among 2,2,3-trimethylbutane or a mixture of 2,2,3-trimethylbutane and 2,3,3-trimethyl-1-butene.

10. The method as set forth in claim 1, wherein the dehydrogenating/hydrogenating function of the catalyst used for coupling is selected from among transition metals from the groups VB, VIB, VIIIB, IB, that are present in the catalyst in the form of oxides, carbonates, halides, phosphates, carbides, nitrides, or as reduced metals.

11. The method as set forth in claim 1, wherein the basic function of the catalyst used for combining is selected from among alkali and alkaline earth metals of groups IA and IIA in the form of oxides, hydroxides, phosphates, carbonates, supported or not supported, on heterogeneous that can include aluminas, hydrotalcites, basic zeolites, silicas, silica-aluminas, activated carbon, mixed oxides, spinels, or basic clays, in addition to anion exchange resins or metal oxides.

12. The method as set forth in claim 1, wherein the catalyst operating used for combining is Cu supported on K-doped alumina.

13. The method as set forth in claim 1, wherein the catalyst operates at a temperature in the range from 150 to 550° C.

14. The method as set forth in claim 1, wherein the catalyst operates with a space velocity (LHSV) of from 0.1 to 10 $h^{-1}$.

15. The method as set forth in claim 1, wherein the catalyst operates at a pressure of from 5 to 200 bar.

16. The method as set forth in claim 1, wherein the catalyst operates with a feed having a volumetric ratio of hydrogen ($H_2$) per oxygenated compound containing six carbons from 0 to 10 mol $H_2$/mol.

17. The method as set forth in claim 1, wherein the catalyst operates at a molar ratio of the oxygenated compound containing one carbon to that of the oxygenated compound containing six carbons of at least 1 to 20 mol:mol.

18. The method as set forth in claim 1, wherein the unreacted methanol during coupling is recovered and returned to the coupling step.

19. The method as set forth in claim 1, wherein the content of hydrogen ($H_2$) used when CO is employed as an oxygenated carbon compound is greater than or equal to 2 mol, and the content of hydrogen ($H_2$) is greater than or equal to 3 mol when the compound with one carbon is $CO_2$.

20. The method as set forth in claim 1, characterized in that the gaseous effluent from the coupling step containing $H_2$, CO, and $CO_2$ is returned to the coupling step.

21. The method as set forth in claim 1, wherein a catalyst used for deoxygenating is a dehydration catalyst with acidic sites.

22. The method as set forth in claim 1, wherein deoxygenating comprises a hydrodeoxygenation reaction in the presence of $H_2$ and a hydrotreatment catalyst, with sulfides of Mo or W, promoted by Ni or Co, and supported on solids.

23. The method as set forth in claim 1, wherein deoxygenating comprises a hydrodeoxygenation reaction in the presence of $H_2$ in which the hydrodeoxygenation catalyst is a partially reduced metal oxide supported on a porous solid.

24. The method as set forth in claim 23, wherein the hydrodeoxygenation catalyst has partially reduced metals in its composition that are selected from among Pt, Pd, Ru, Ni, Cu, Mo, W, Co, Ir, Rh, Au, Ce, Fe, Mn, Ga, Pb, and Bi, alone or in mixtures, and supported on solids selected from alumina, silicas, silica-aluminas, zeolites, hydrotalcites, mixed oxides, spinels, MgO, $TiO_2$, ZnO, $CeO_2$, phosphates, resins sulfonic compounds, $ZrO_2$, sulfated Zr, carbon, and activated carbon.

25. The method as set forth in claim 23 wherein the hydrodeoxygenation catalyst support is oxophilic.

* * * * *